United States Patent
Klinghoffer et al.

(10) Patent No.: US 10,150,721 B2
(45) Date of Patent: Dec. 11, 2018

(54) CATALYTIC MEMBRANE REACTOR FOR DIMETHYL ETHER SYNTHESIS FROM CARBON DIOXIDE AND HYDROGEN

(71) Applicant: GAS TECHNOLOGY INSTITUTE, Des Plaines, IL (US)

(72) Inventors: Naomi Klinghoffer, Chicago, IL (US); Shiguang Li, Mount Prospect, IL (US)

(73) Assignee: GAS TECHNOLOGY INSTITUTE, Des Plaines, IL (US)

( * ) Notice: Subject to any disclaimer, the term of this patent is extended or adjusted under 35 U.S.C. 154(b) by 0 days.

(21) Appl. No.: 15/467,068

(22) Filed: Mar. 23, 2017

(65) Prior Publication Data
US 2018/0016218 A1 Jan. 18, 2018

Related U.S. Application Data

(60) Provisional application No. 62/362,644, filed on Jul. 15, 2016.

(51) Int. Cl.
| | | |
|---|---|---|
| *C07C 41/09* | (2006.01) |
| *B01J 19/24* | (2006.01) |
| *B01J 29/70* | (2006.01) |
| *B01J 35/06* | (2006.01) |
| *C07C 29/153* | (2006.01) |
| *C07C 41/01* | (2006.01) |

(52) U.S. Cl.
CPC ........... *C07C 41/09* (2013.01); *B01J 19/2475* (2013.01); *B01J 29/7003* (2013.01); *B01J 35/065* (2013.01); *C07C 29/153* (2013.01); *C07C 41/01* (2013.01); *B01J 2219/24* (2013.01)

(58) Field of Classification Search
CPC .... C07C 41/09; C07C 29/153; B01J 19/2475; B01J 29/7003; B01J 35/065
USPC ........................................................ 568/698
See application file for complete search history.

(56) References Cited

U.S. PATENT DOCUMENTS

| | | | |
|---|---|---|---|
| 5,935,533 A | 8/1999 | Kleefisch et al. | |
| 7,550,121 B2 * | 6/2009 | Mori ..................... | B01D 53/228 210/321.6 |
| 2004/0064002 A1 | 4/2004 | Lee et al. | |
| 2004/0198847 A1 | 10/2004 | Hojlund Nielsen et al. | |
| 2013/0035406 A1 * | 2/2013 | Randhava ............... | C07C 41/09 518/705 |
| 2015/0018582 A1 | 1/2015 | Schodel et al. | |

OTHER PUBLICATIONS

Ghosh et al., "Comparative study on treatment of kitchen-sink wastewater using single and multichannel ceramic membrane" in Int. J. Environmental Technology and Management, 2010, 13, 336-347.*
PCT International Search Report, Form PCT/ISA/210, dated Aug. 14, 2017, (2 pages).
PCT Written Opinion of the International Searching Authority, Form PCT/ISA/237, dated Aug. 14, 2017, (4 pages).

* cited by examiner

*Primary Examiner* — Clinton A Brooks
*Assistant Examiner* — Kofi Adzamli
(74) *Attorney, Agent, or Firm* — Pauley Erickson & Kottis

(57) ABSTRACT

Methods and systems or devices for synthesis of dimethyl ether (DME) from carbon dioxide and hydrogen are provided. A high surface area hollow fiber catalytic membrane reactor such as with hollow fibers coated with a water permeable membrane material is used. The reactor also contains a bi-functional methanol synthesis component and dehydration catalyst component such that the two-step reaction takes place on the catalyst surface. Produced water permeates through the membrane, exiting the reactor immediately after it is formed. Unreacted reactants and products flow to the reactor exit.

8 Claims, 4 Drawing Sheets

CATALYTIC MEMBRANE REACTOR FOR DIMETHYL ETHER SYNTHESIS FROM CARBON DIOXIDE AND HYDROGEN

CROSS REFERENCE TO RELATED APPLICATION

This application claims the benefit of U.S. Provisional Patent Application Ser. No. 62/362,644, filed on 15 Jul. 2016. The Provisional application is hereby incorporated by reference herein in its entirety and is made a part hereof, including but not limited to those portions which specifically appear hereinafter.

BACKGROUND OF THE INVENTION

Field of the Invention

This development relates generally to methods and systems or devices for synthesis of dimethyl ether (DME) from carbon dioxide and hydrogen. More particularly, this development relates to devices and methods that utilize a multi-channel catalytic membrane reactor having, containing or including a bi-functional catalyst for synthesis of dimethyl ether.

Discussion of Related Art

U.S. Publication No. 2004/0064002 discloses a method for preparing dimethyl ether from methanol using a membrane reactor for separation and reaction.

U.S. Publication No. 2015/0018582 discloses a process for preparing dimethyl ether from synthesis gas. This process is a two-step process that includes a synthesis step, wherein synthesis gas comprising hydrogen and carbon monoxide is converted into dimethyl ether and carbon dioxide, and a separation step, wherein unconverted synthesis gas is separated from carbon dioxide by a membrane.

Other processes are currently being developed for dimethyl ether production from carbon dioxide and hydrogen. However, these processes do not employ membrane reactors and are subject to issues arising from excess water, such as including reduced conversion and catalyst deactivation, for example.

SUMMARY OF THE INVENTION

The subject development comprises methods and systems or devices for improved synthesis of dimethyl ether (DME) from carbon dioxide and hydrogen.

In a preferred embodiment, the invention includes a hollow fiber catalytic membrane reactor that utilizes a bi-functional catalyst for a one-step synthesis of dimethyl ether from carbon dioxide and hydrogen, preferably renewable hydrogen.

In accordance with one aspect of the subject development, a system for synthesis of dimethyl ether from carbon dioxide and hydrogen is provided. In one embodiment, such a system includes a catalytic membrane reactor including or containing a plurality of channels and having an outer surface with a water permeable membrane coating. The reactor further contains a bi-functional catalyst material including a methanol synthesis catalyst component and a dehydration catalyst component. The methanol synthesis catalyst component desirably serves to catalyze reaction of carbon dioxide and hydrogen to form methanol and water. The dehydration catalyst component desirably serves to catalyze dehydration of methanol to form dimethyl ether and water. In the system, upon formation formed water permeates through the water permeable membrane coating and exits the reactor.

In accordance with one aspect of the development, the catalytic membrane reactor comprises at least one reactor body including at least two such channels.

In one embodiment, each of the channels includes an inner surface or volume and an outer surface or volume, wherein the hi-functional catalyst material is disposed on or in the inner surface or volume of the channels and wherein formed water permeates through the reactor body and the water permeable membrane coating to a shell side of the reactor.

In accordance with another aspect of the development, the catalytic membrane reactor comprises a plurality of hollow fibers, each fiber forming at least one such channel.

In accordance with one embodiment, the catalytic membrane reactor contains a plurality of hollow fibers each having a water permeable membrane coating.

In one embodiment, each of the hollow fibers includes an inner surface or volume and an outer surface or volume, wherein the bi-functional catalyst material is disposed on or in the outer surface or volume of the hollow fibers and wherein formed water permeates through the water permeable membrane coating and the hollow fiber and passes in the inner volume of the hollow fibers.

In one embodiment, a system for synthesis of dimethyl ether from carbon dioxide and hydrogen is provided where the system includes a catalytic membrane reactor containing a plurality of hollow ceramic fibers. The hollow ceramic fibers have an outer surface with a water permeable membrane coating comprising NaA zeolite membrane. The reactor further contains a bi-functional catalyst material including a methanol synthesis catalyst component to catalyze reaction of carbon dioxide and hydrogen to form methanol and water and a dehydration catalyst component to catalyze dehydration of methanol to form dimethyl ether. The methanol synthesis catalyst component desirably includes at least one of copper, zinc oxide and alumina. The dehydration catalyst component desirably includes silica and alumina. Upon formation, water formed by or in the reactor desirably permeates through the water permeable membrane coating and exits the reactor.

In another embodiment, a system for synthesis of dimethyl ether from carbon dioxide and hydrogen is provided where the system includes a multi-channel ceramic catalytic membrane reactor. The multi-channel ceramic catalytic membrane reactor includes at least one of: a) at least one ceramic reactor body including at least two hollow channels, with the at least one ceramic reactor body having an outer surface with a water permeable membrane coating of or including NaA zeolite membrane and b) a plurality of hollow ceramic fibers, each ceramic fiber forming at least one hollow channel, with the hollow ceramic fibers having an outer volume with a water permeable membrane coating of or including NaA zeolite membrane.

The reactor further contains a bi-functional catalyst material including a methanol synthesis catalyst component to catalyze reaction of carbon dioxide and hydrogen to form methanol and water, and a dehydration catalyst component to catalyze dehydration of methanol to form dimethyl ether. The methanol synthesis catalyst component can desirably include at least one of copper, zinc oxide and alumina. The dehydration catalyst component can desirably include silica, alumina or a combination thereof. Upon formation, water formed by or in the reactor desirably permeates through the water permeable membrane coating and exits the reactor.

In another aspect of the subject development, a method for forming dimethyl ether from carbon dioxide and hydrogen is provided. In accordance with one embodiment such a method involves introducing carbon dioxide and hydrogen into a multi-channel ceramic catalytic membrane reactor at dimethyl ether synthesis conditions to form dimethyl ether. The catalytic membrane reactor desirably has or includes an outer surface with a water permeable membrane coating. The catalytic membrane reactor further contains or includes a bi-functional catalyst material including a methanol synthesis catalyst component to catalyze reaction of carbon dioxide and hydrogen to form methanol and water and a dehydration catalyst component to catalyze dehydration of methanol to form dimethyl ether. The reactor operates such that, upon formation, formed water permeates through the water permeable membrane coating and exits the reactor.

Other objects and advantages will be apparent to those skilled in the art from the following detailed description taken in conjunction with the appended claims and drawings.

DETAILED DESCRIPTION

As detailed below, the subject development is generally directed to methods and systems or devices for improved synthesis of dimethyl ether (DME) from carbon dioxide and hydrogen.

In a preferred embodiment, the subject development involves or includes a hollow fiber catalytic membrane reactor that uses or employs a bi-functional catalyst material for one-step synthesis of dimethyl ether from carbon dioxide and hydrogen, preferably renewable hydrogen.

In accordance with a preferred aspect of the subject development, two primary reactions (shown in Equations 1 and 2, below) occur in synthesis of dimethyl ether from carbon dioxide and hydrogen:

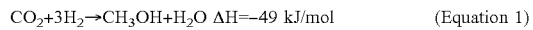
(Equation 1)

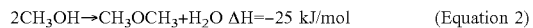
(Equation 2)

The first reaction comprises methanol synthesis from carbon dioxide and hydrogen, which is advantageously conducted using, by or in the presence of a methanol synthesis catalyst. The second reaction comprises dehydration of methanol to dimethyl ether, which is advantageously conducted using, by or in the presence of a dehydration catalyst.

As detailed below, the subject development desirably employs a bi-functional catalyst material including a methanol synthesis catalyst component to catalyze the reaction of carbon dioxide and hydrogen to form methanol and water (i.e., above Equation 1) and a dehydration catalyst component to catalyze dehydration of methanol to form dimethyl ether (i.e., above Equation 2).

In an embodiment, the methanol synthesis catalyst component of the bi-functional catalyst material may include one or more of copper, zinc, zinc oxide, alumina and silica.

In an embodiment, the dehydration catalyst component of bi-functional catalyst material preferably comprises a solid acid catalyst with primary components including silica and alumina. In accordance with certain embodiments, suitable dehydration catalyst components can include one or more of zeolites (e.g., aluminosilicates), SAPO-34, sulfated zirconia, tungsten zirconia copper and iron additives. The dehydration catalyst may also include one or more catalyst promoters. Suitable such promoters in accordance with one embodiment include phosphate catalyst promoters, such as one or more phosphorus oxides, such as $P_2O_5$, for example. In another embodiment, sodium may serve as a useful promoter.

In a preferred embodiment, the reactions occur in a high surface area hollow fiber membrane reactor that is permeable to water. In an embodiment, the membrane comprises a zeolite NaA material and includes multi-channel fibers with each channel internally coated with the bi-functional catalyst material. The two reactions take place on the catalyst surface. Water permeates through the membrane, exiting the reactor immediately after it is formed. Unreacted reactants and products continue to flow through the channel.

Figure 1:
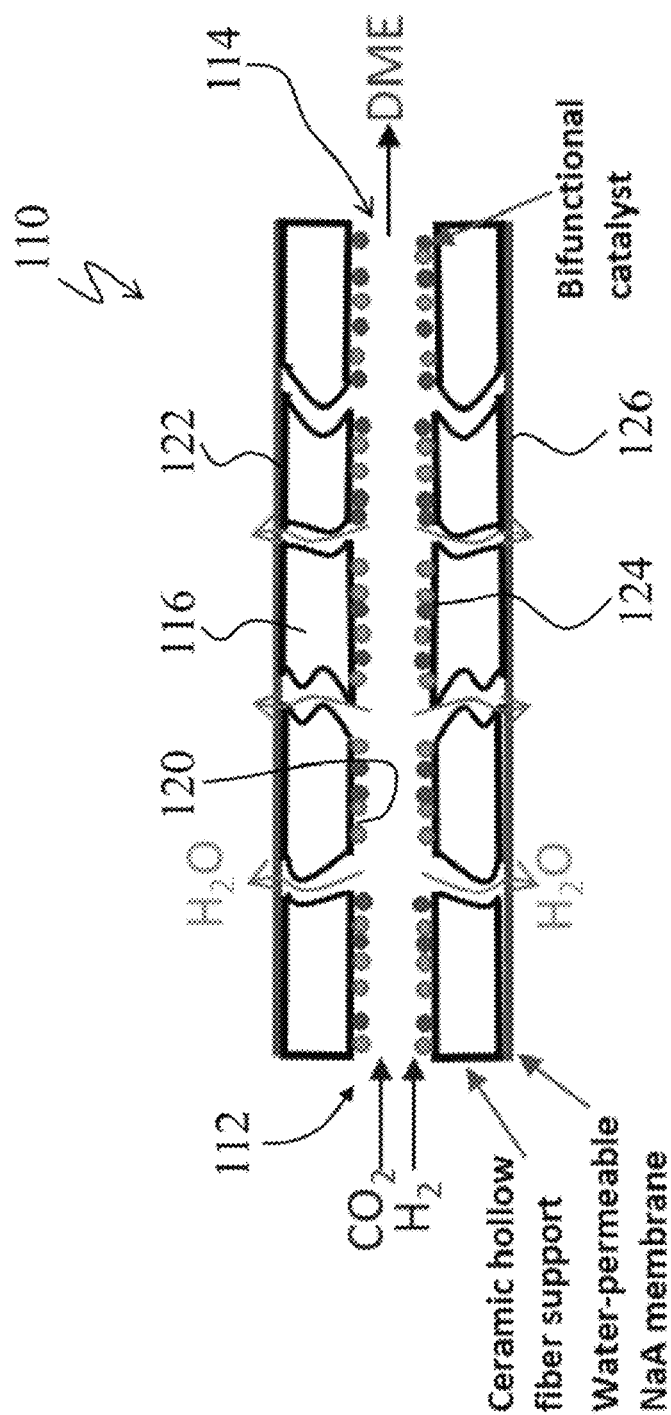
FIG. 1 is a simplified schematic of a dimethyl ether synthesis catalytic membrane reactor system in accordance with one embodiment of the subject development.

Turning to FIG. 1 there is shown a simplified schematic of a dimethyl ether synthesis catalytic membrane reactor system, generally designated by the reference numeral 110, in accordance with one embodiment of the subject development. The dimethyl ether synthesis catalytic membrane reactor system 110 includes an entrance or inlet 112 and an exit or outlet 114 and is generally composed of a porous ceramic hollow fiber support 116 having an inner surface 120 and an outer surface 122.

As shown, the inner surface 120 can desirably be coated with or otherwise have appropriately disposed thereon the bi-functional catalyst material 124, such as described above. The outer surface 122 can desirably be coated with or otherwise have appropriately disposed thereon a water permeable membrane coating 126 such as composed of NaA zeolite membrane.

Those skilled in the art and guided by the teachings herein provided will understand and appreciate that the broader practice of the subject development is not necessarily limited to or requires practice with specific or particular water permeable membrane coatings. In accordance with other embodiments, suitable water permeable membrane coatings for use in the practice of the subject development may, for example, include but not necessarily limited to one or more hydrophilic zeolites (such as zeolite X, zeolite Y, zeolite T, mordenite, zeolite beta, ZSM-5, ZSM-11, Ferrierite, Zeolite SOD, for example), hydrophilic metal organic frameworks (MOFs, such as MOF-8, for example), high-temperature polymers (such as poly (ether ether ketone), and polybenzimidazole, for example), graphite, graphite oxide, and combinations of these materials.

Carbon dioxide and hydrogen are introduced into the dimethyl ether synthesis catalytic membrane reactor system 110 at the entrance 112. The two reactions take place on the catalyst surface 124. Water, such as formed or produced during the DME synthesis, permeates through the membrane 126, exiting the reactor 110 immediately after it is formed. The product (DME) as well as unreacted reactants continue to flow through the channel and exit via the outlet 114.

In one preferred embodiment, the hydrogen is preferably renewable hydrogen as, for example, hydrogen from renewable energy has or produces the added benefit of producing renewable fuel.

While FIG. 1 illustrates a dimethyl ether synthesis catalytic membrane reactor system composed of a single channel, the broader practice of the subject development is not necessarily so limited as reactors with multiple or plurality of channels (e.g., such as having 2, 3, 4 or more channels) can be appropriately utilized and preferred in alternative embodiments.

As detailed below, suitable systems for synthesis of dimethyl ether from carbon dioxide and hydrogen in accordance with a preferred aspect of the subject development include a catalytic membrane reactor including a plurality of channels and having an outer surface with a water permeable membrane coating. The reactor further includes or contains the bi-functional catalyst material, such as identified above, and including a methanol synthesis catalyst component to catalyze reaction of carbon dioxide and hydrogen to form methanol and water and a dehydration catalyst component to catalyze dehydration of methanol to form dimethyl ether. Upon formation, the formed water permeates through the water permeable membrane coating and exits the reactor. In particular embodiments, the catalytic membrane reactor includes at least one of: a) at least one reactor body including at least two of the channels and b) a plurality of hollow fibers, each fiber forming at least one of the channels.

Figures 2, 3:
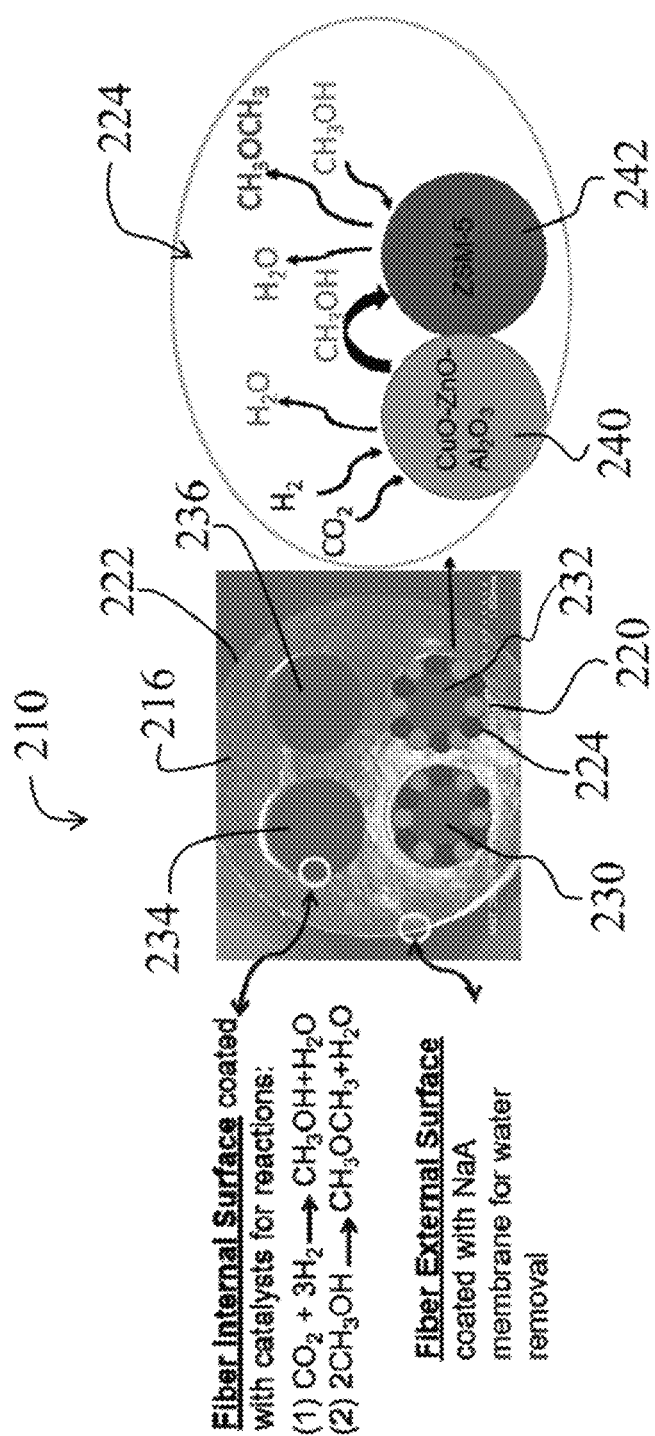
FIG. 2 is a simplified cross sectional view of a four channel fiber reactor or element for dimethyl ether synthesis in accordance with one embodiment of the subject development.
FIG. 3 is a simplified schematic representation depicting the components of the bi-functional catalyst, in accordance with one embodiment of the subject development, and the reactions respectively taking place thereon or associated therewith.

FIG. 2 illustrates a four channel dimethyl ether synthesis catalytic membrane reactor system or element 210 for dimethyl ether synthesis in accordance with one embodiment of the subject development.

The four channel fiber reactor or element 210 is similar to the dimethyl ether synthesis catalytic membrane reactor system 110 described above in that it includes a ceramic hollow fiber support 216 having an outer surface 222 such as desirably coated or otherwise having appropriately disposed thereon a water permeable membrane coating.

However, rather than being composed of a single channel, the porous ceramic hollow fiber support 216 includes four channels 230, 232, 234, and 236. The inner surface 220 of one or more and in some preferred embodiments, each of the channels 230, 232, 234, and 236, is desirably coated or otherwise has appropriately disposed thereon a bi-functional catalyst material 224, such as described above. In FIG. 2, only channels 230 and 232 are shown as including the catalyst material 224.

Similar to the dimethyl ether synthesis catalytic membrane reactor system 110 described above, carbon dioxide and hydrogen, preferably renewable hydrogen are introduced into the dimethyl ether synthesis catalytic membrane reactor system 210, such as at an entrance (not shown) at one end. The two reactions take place on the catalyst surface 224. Water permeates through the membrane coating disposed on the outer surface 222, exiting the reactor 210 immediately after it is formed. The product (DME) as well as unreacted reactants continue to flow through the channel and exit, such as via an outlet (not shown) disposed at an opposite end of the reactor 210.

FIG. 3 is a simplified schematic representation depicting the components of the hi-functional catalyst, in accordance with one embodiment of the subject development, and the reactions respectively taking place thereon or associated therewith. More particularly, FIG. 3 depicts the bi-functional catalyst material 224 such as disposed on the fiber internal surface of the four channel dimethyl ether synthesis catalytic membrane reactor system 210 shown in FIG. 2.

The bi-functional catalyst material 224 includes a methanol synthesis catalyst or component 240 effective for or to catalyze the reaction of carbon dioxide and hydrogen to form methanol and a dehydration catalyst or component 242 effective for or to catalyze dehydration of methanol and the formation of dimethyl ether. As shown water ($H_2O$) is a by-product of each of these reactions. In accordance with a preferred practice of an aspect of the subject development, such by-product water desirably permeates through the membrane coating disposed on the outer surface 222, exiting the reactor 210 immediately after it is formed.

Figures 4, 5:
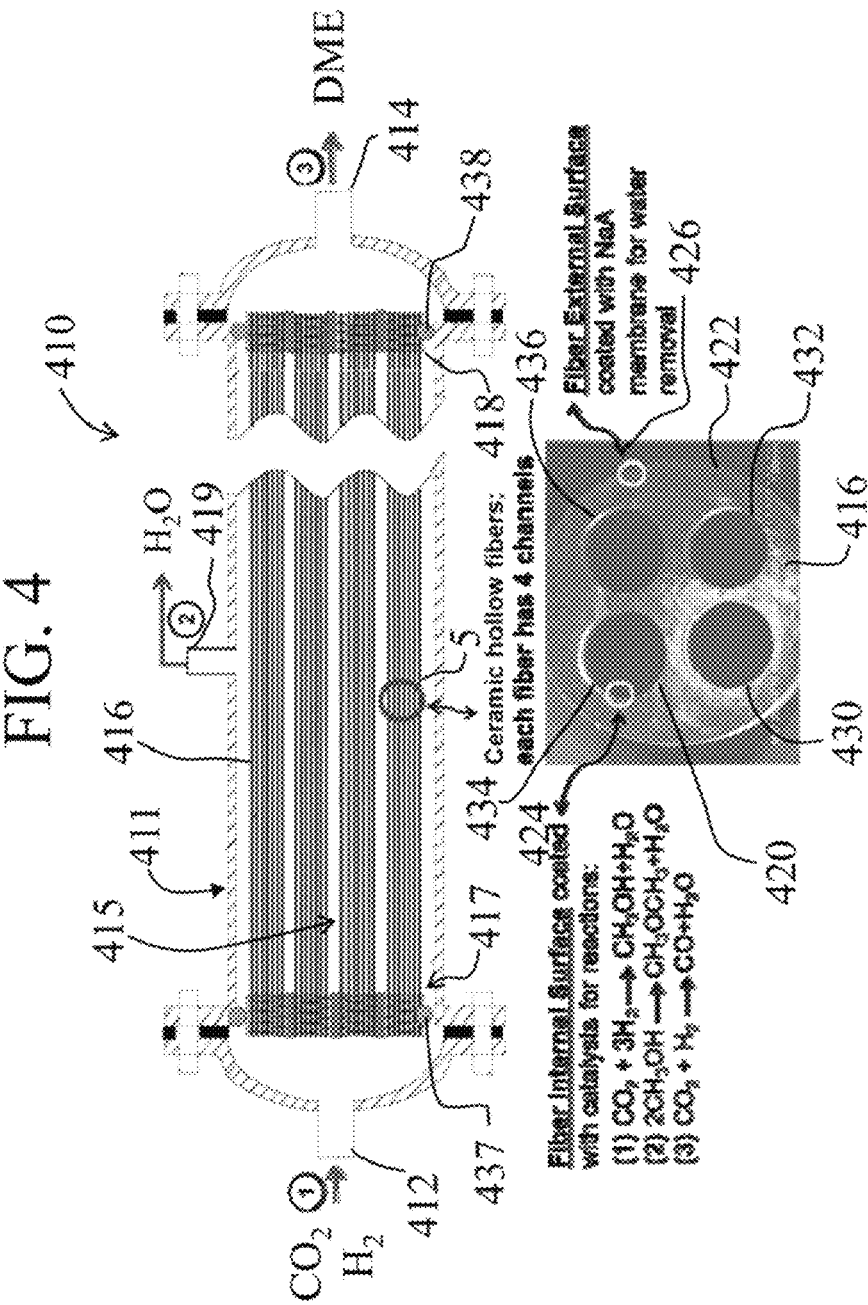
FIG. 4 is a simplified fragmentary schematic of a dimethyl ether synthesis catalytic membrane reactor system in accordance with another embodiment of the subject development.
FIG. 5 is a simplified schematic detailed sectional view of one of the ceramic hollow fibers of the dimethyl ether synthesis catalytic membrane reactor system shown in FIG. 4 viewed at circle 5 of FIG. 4.

FIG. 4 illustrates a dimethyl ether synthesis catalytic membrane reactor system 410 in accordance with another embodiment of the subject development.

The reactor 410 includes a housing or shell 411 having an inlet 412 and an outlet 414 disposed on opposite axial ends of the housing. Within the housing 411 there is contained an array 415 of axially extending ceramic hollow fibers 416. The fibers 416 have a first end 417 disposed at or adjacent the inlet 412 and an opposite end 418 disposed at or adjacent the outlet 414.

In accordance with one embodiment, the inlet 412 can desirably serve for the introduction of carbon dioxide and water into the reactor 410 and the outlet 414 can desirably serve for removal of dimethyl ether from the reactor 410.

As shown in FIG. 5, each of the fibers 416 includes four hollow channels 430, 432, 434, and 436. As with the previously described embodiments, the channels each have or include an inner surface 420 such as whereupon a bi-functional catalyst material coating 424 such as described above is preferably disposed. The fibers have or include an outer surface 422 such as whereupon a water permeable membrane coating 426 such as described above is preferably disposed.

As shown in FIG. 4, in addition to the inlet 412 and the outlet 414 disposed on opposite axial ends, the housing 411 also desirably includes a peripheral side outlet 419 such that water formed during reactions 1 and 2 can desirably be expeditiously removed. Further, the reactor 410 can desirably include seals or gaskets 437 and 438, such as disposed at or near the ends 417 and 418 of the axially extending ceramic hollow fiber array 415, to ensure that there is separation between the tube side (e.g., the inside of the tubes) and the shell side (e.g., outside of the tubes) and thus limit and restrict flow or access to the shell side to material conveyed thereto through the membrane 426.

While the subject development has been described above making specific reference to embodiments wherein a bi-functional catalyst material such as herein provided, is disposed on an inner surface of a fiber inner hollow or inner channel of the respective hollow fiber structure such as in the form of a coating, those skilled in the art and guided by the teachings herein provided will understand and appreciate that the broader practice of the subject development is not necessarily so limited.

Figure 6:
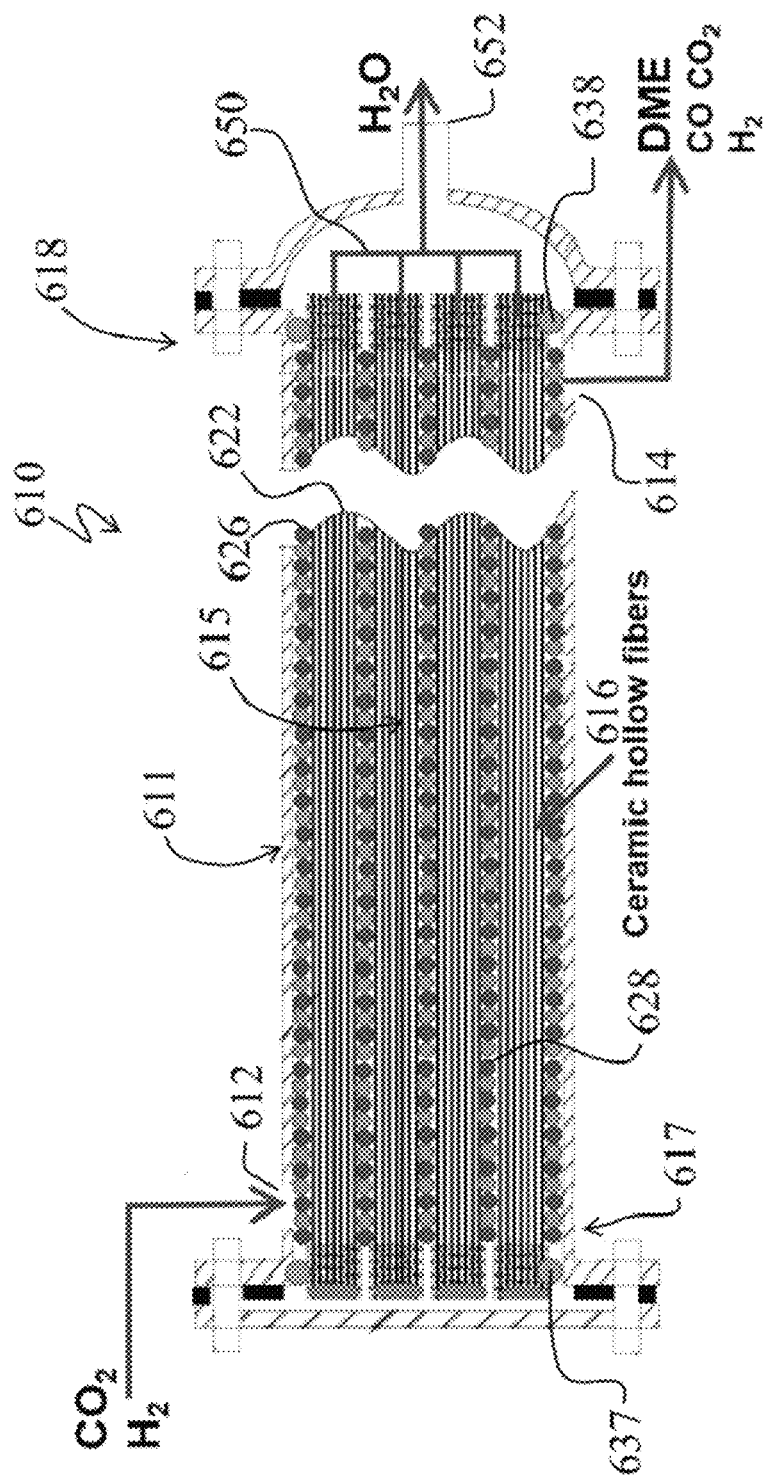
FIG. 6 is a simplified schematic of a dimethyl ether synthesis catalytic membrane reactor system in accordance with another embodiment of the subject development.

For example, FIG. 6 illustrates a dimethyl ether synthesis catalytic membrane reactor system 610 in accordance with another embodiment of the subject development generally composed of a plurality of water permeable membrane coated multi-channel fibers with a bi-functional catalyst material such as herein described packed on the shell side of the fibers.

The reactor 610 includes a housing or shell 611 having an inlet 612 at or adjacent a first end 617 and an outlet 614 at or adjacent a second end 618, generally opposite the first end 617. Within the housing 611 there is contained an array 615 of axially extending ceramic hollow fibers 616 generally extending between the first end 617 and the second end 618. Further, similar to the reactor 410 described above, the reactor 610 can desirably include seals or gaskets 637 and 638, such as disposed at or near the ends 617 and 618 of the axially extending ceramic hollow fiber array 615, to ensure that there is separation between the tube side (e.g., the inside of the hollow fibers) and the shell side (e.g., outside of the hollow fibers) and thus limit and restrict flow or access to the tube side to material conveyed thereto through the hollow fibers 616.

Similar to the fibers 416 shown in FIGS. 4 and 5, the fibers 616 have or include an outer surface such as whereupon a water permeable membrane coating, such as described above, is preferably disposed. In the reactor embodiment 610, however, the bi-functional catalyst material such as herein described rather than coating or otherwise being internally disposed therein is included as a packing 628 within the reactor housing 611 and in which the fibers 616 are disposed.

Operation of the dimethyl ether synthesis catalytic membrane reactor system 610 in accordance with one aspect of the subject development can desirably involve, feeding a mixture of $CO_2$ and $H_2$ into the reactor 610 such as via the inlet 612. The catalytic membrane reactor 610 contains a bi-functional catalyst 628, such as described above, in the outside volume (e.g., the shell side of the reactor) of the hollow fibers 616 (e.g., $Al_2O_3$) for DME production. The product DME as well as unreacted feed materials and non-water by-products exit the reactor via the outlet 614. To improve conversion and catalyst performance, produced water is desirably removed in situ, e.g., through the NaA zeolite membrane 626 coated on the external surface 622 of the hollow fibers 616, with the water passing into the channels and then along the channels to a channel discharge volume, schematically shown and identified as 650, and out a channel discharge exit 652.

The above-described FIG. 3 simplified schematic representation depicting the components of the bi-functional catalyst, in accordance with one embodiment of the subject development, and the reactions respectively taking place thereon or associated therewith can be here applied, however, now with the bi-functional catalyst material disposed in the outside volume (e.g., the shell side of the reactor) of the hollow fibers 616. The bi-functional catalyst material includes a methanol synthesis catalyst or component effective for or to catalyze the reaction of carbon dioxide and hydrogen to form methanol and a dehydration catalyst or component effective for or to catalyze dehydration of methanol and the formation of dimethyl ether. Water ($H_2O$) is a by-product of each of these reactions. In accordance with a preferred practice of an aspect of the subject development, such by-product water desirably permeates through the membrane into the channels and then out of the reactor exit.

The subject development can desirably address or resolve at least two long standing problems related to fuel synthesis from carbon dioxide and hydrogen: (1) known processes have thermodynamic limitations which reduce overall conversion; and (2) in known processes, water adsorbs to the catalyst surface, decreasing catalyst performance.

With regards to the first issue, thermodynamic limitations have typically imposed an upper bound on the maximum conversion that can be achieved in a single pass using known methods of methanol synthesis from carbon dioxide and hydrogen. However, with the subject development, combining a methanol synthesis catalyst with a dehydration or DME synthesis catalyst can desirably serve to improve thermodynamics, such as to produce or result in improved rates of conversion. For example, application and practice of the subject development, in accordance with different embodiments, may desirably produce or result in an increase in conversion (at 60 psi) based on equilibrium calculations of 10%, 20%, 30%, or, in some cases 40% or more.

As will be appreciated, doing the methanol synthesis and dehydration reactions as a one step process results or means that additional water will be present (compared to doing just one of the two reactions), since water is generated in both steps. Thus, removal of water reaction product in situ, as done in the subject development, can be significant, if not critical, and can desirably lead to further improved process thermodynamics. In contrast, in known processes this reaction is typically done with synthesis gas, or as a two-step process. In the case where synthesis gas, having a high CO fraction, is used, there can be half as much water present in the system compared to when the reaction is done with $CO_2$. Therefore, processing with $CO_2$ necessitates the incorporation and utilization of effective and efficient appropriate water management.

With regards to the second issue, water is known to strongly adsorb onto the catalyst surface. Such absorption can act to block active sites for methanol dehydration, resulting in decreased catalyst performance. When water molecules occupy acid sites on γ-Alumina, Lewis acid sites can be transformed to Brönsted acid sites, which are substantially weaker. Water is known to affect catalyst performance, and in the case of DME synthesis from methanol, the reaction rate decreases exponentially with increased presence of water (Sierra et al. Chem. Eng. Trans., 2013, 32, 613). Jun et al. used a γ-$Al_2O_3$ catalyst for DME synthesis from methanol and saw a drop in performance by approximately 50% once water was introduced (Jun et al. Bull. Korean. Chem. Soc., 2002 23(6) 803). Therefore, removal of water can be critical to enabling long term performance with minimal catalyst deactivation.

In the subject development, the incorporation and utilization of hollow fibers having an outer surface with a water permeable membrane coating such that produced water permeates through the membrane, exiting the reactor immediately after it is formed can produce or result in desired effective and efficient appropriate water management.

The subject development has the potential to produce or result in higher product yields and longer catalyst lifetimes, which will decrease overall process costs. The subject development utilizes a unique hollow fiber membrane reactor which has a very high selectivity for water, and a high surface area to volume ratio to allow for easy transport of water out of the reactor.

As identified above, the subject development includes a configuration wherein the reactor consists of hollow fibers with the bi-functional catalyst coated on the inside of the channels and a water selective membrane coated on the outside of the fibers. In such a configuration, water permeates desirably through the channels to the shell side and exits the reactor. In such configuration, the catalyst coating on the inside of the hollow fibers allows for high surface area of available catalyst with low pressure drop in the reactor.

The subject development also includes a configuration wherein $CO_2$ is mixed with $H_2$, and both are fed to a catalytic membrane reactor containing a bi-functional catalyst in the outside volume of hollow fibers (shell side of the reactor) for DME production. To improve conversion and catalyst performance, produced water is removed in situ through a water permeable membrane coated on the external surface of the hollow fibers. The water passes to the inside of the hollow fibers and exits the reactor.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

The claims are not intended to include, and should not be interpreted to include, means-plus- or step-plus-function limitations, unless such a limitation is explicitly recited in a given claim using the phrase(s) "means for" or "step for," respectively.

The invention illustratively disclosed herein suitably may be practiced in the absence of any element, part, step, component, or ingredient which is not specifically disclosed herein.

What is claimed is:

1. A method for forming dimethyl ether from carbon dioxide and hydrogen, the method comprising:
   introducing carbon dioxide and hydrogen into a multi-channel hollow fiber ceramic catalytic membrane reactor at dimethyl ether synthesis conditions to form dimethyl ether, the catalytic membrane reactor comprising a hollow fiber having an outer surface with a water permeable membrane coating, the catalytic membrane reactor further containing a bi-functional catalyst material including a methanol synthesis catalyst component to catalyze reaction of carbon dioxide and hydrogen to form methanol and water and a dehydration catalyst component to catalyze dehydration of methanol to form dimethyl ether and water,
   wherein upon formation formed water permeates through the water permeable membrane coating and exits the reactor.

2. The method of claim 1 wherein the multi-channel, ceramic catalytic membrane reactor comprises at least one of: a) at least one reactor body including at least two of said channels and b) a plurality of hollow fibers, each fiber forming at least one of said channels.

3. The method of claim 2 wherein the multi-channel ceramic catalytic membrane reactor comprises at least one reactor body having at least two of said channels and wherein the at least one reactor body has an outer surface with the water permeable membrane coating.

4. The method of claim 2 wherein the multi-channel ceramic catalytic membrane reactor comprises a plurality of hollow fibers, each fiber forming at least one of said channels.

5. The method of claim 4 wherein each of the hollow fibers includes an inner surface and an outer surface, wherein the bi-functional catalyst material is disposed on the inner surface of the hollow fibers and the water permeable membrane coating is disposed on the outer surface of the hollow fibers, and wherein formed water permeates through the fibers and the water permeable membrane coating disposed thereon to a shell side of the reactor.

6. The method of claim 4 wherein each of the hollow fibers includes an inner volume and an outer volume, wherein the bi-functional catalyst material is disposed in the outer volume of the hollow fibers and wherein formed water permeates through the water permeable membrane coating and the hollow fiber and passes in the inner volume of the hollow fibers.

7. The method of claim 2 wherein the water permeable membrane coating comprises NaA zeolite membrane.

8. The method of claim 2 wherein the multi-channel ceramic catalytic membrane reactor comprises $Al_2O_3$.

* * * * *